(12) United States Patent
Dow et al.

(10) Patent No.: US 9,357,978 B2
(45) Date of Patent: *Jun. 7, 2016

(54) THREE DIMENSIONAL FETAL HEART IMAGING BY NON-ECG PHYSIOLOGICAL GATED ACQUISITION

(75) Inventors: Alasdair Dow, Snohomish, WA (US); Antoine Collet-Billon, Paris (FR); James Jago, Seattle, WA (US); Lisa Kay Pumphrey, Bothell, WA (US); Paul R. Detmer, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 206 days.

This patent is subject to a terminal disclaimer.

(21) Appl. No.: 13/379,764

(22) PCT Filed: Jun. 2, 2010

(86) PCT No.: PCT/IB2010/052469
§ 371 (c)(1),
(2), (4) Date: Feb. 2, 2012

(87) PCT Pub. No.: WO2011/001309
PCT Pub. Date: Jan. 6, 2011

(65) Prior Publication Data
US 2012/0123267 A1   May 17, 2012

Related U.S. Application Data

(60) Provisional application No. 61/221,885, filed on Jun. 30, 2009.

(51) Int. Cl.
*A61B 8/14* (2006.01)
*A61B 8/08* (2006.01)
(Continued)

(52) U.S. Cl.
CPC ............... *A61B 8/0866* (2013.01); *A61B 8/02* (2013.01); *A61B 8/483* (2013.01); *G01S 15/8993* (2013.01); *A61B 8/06* (2013.01); *A61B 8/543* (2013.01)

(58) Field of Classification Search
CPC combination set(s) only.
See application file for complete search history.

(56) References Cited

U.S. PATENT DOCUMENTS

| | | |
|---|---|---|
| 5,099,847 A | 3/1992 | Powers |
| 5,170,791 A | 12/1992 | Boos |

(Continued)

FOREIGN PATENT DOCUMENTS

| | | |
|---|---|---|
| JP | 2009119250 A | 4/2009 |
| WO | 9502361 A1 | 1/1995 |
| WO | 2008071454 A2 | 6/2008 |

OTHER PUBLICATIONS

Brekke et al., Tissue Doppler gated (TDOG) dynamic three-dimensional ultrasound imaging of the fetal heart, Journal of Ultrasound in Obstetrics & Gynecology, vol. 24, pp. 192-198, 2004.*

Deng et al. "Real-Time Three-Dimensional Fetal Echocardiography-Optimal Imaging Windows", Ultrasound in Med. & Biol., vol. 28, No. 9, pp. 1099-1105, 2002.*

(Continued)

*Primary Examiner* — Katherine Fernandez
*Assistant Examiner* — Farshad Negarestan

(57) ABSTRACT

An ultrasonic diagnostic imaging system acquires 3D data sets of the fetal heart by use of a gating signal synthesized from detected motion of the fetal heart. A sequence of temporally different echo signals are acquired from a location in the anatomy where motion representative of the heart cycle is to be estimated, such as a sample volume in the fetal carotid artery or an M line through the fetal myocardium. A heart cycle signal is synthesized from the detected motion and used to gate the acquisition of fetal heart image data at one or more desired phases of the fetal heart cycle. In an illustrated embodiment 3D data sets are acquired from multiple subvolumes, each over the full fetal heart cycle, then combined to produce a live 3D loop of the beating fetal heart.

13 Claims, 5 Drawing Sheets

(51) Int. Cl.
*A61B 8/02* (2006.01)
*G01S 15/89* (2006.01)
*A61B 8/06* (2006.01)
*A61B 8/00* (2006.01)

(56) References Cited

U.S. PATENT DOCUMENTS

| | | | |
|---|---|---|---|
| 5,993,390 A | 11/1999 | Savord | |
| 5,997,479 A * | 12/1999 | Savord et al. | 600/447 |
| 6,436,048 B1 | 8/2002 | Pesque | |
| 6,966,878 B2 | 11/2005 | Schoisswohl | |
| 7,261,695 B2 * | 8/2007 | Brekke et al. | 600/443 |
| 8,565,504 B2 | 10/2013 | Abe | |
| 2004/0092816 A1 | 5/2004 | Ossmann et al. | |
| 2007/0167809 A1 | 7/2007 | Dala-Krishna | |

OTHER PUBLICATIONS

Deng, J. et al., "Simultaneous use of two ultrasound scanners for motion-gated three-dimensional fetal echocardiography," Ultrasound in Medicine and Biology, NY, NY, US LINKD- DOI:10.1016/S0301-5629(00)00220-9, vol. 26, No. 6, Jul. 1, 2000, pp. 1021-1032, XP04295636.

Deng, J. et al., "Online motion-gated dynamic three-dimensional echocardiography in the fetus-preliminary results," Ultrasound in Medicine and Biology, NY, NY, US LNKD- DOI:10.1016/20301-5629(00)00313-6, vol. 27, No. 1, Jan. 1, 2001, pp. 43-50, XP004295663.

Deng, J. et al., "Conversion of umbilical arterial Doppler waveforms to cardiac cycle triggering signals: a preparatory study for online motion-gated three-dimensional fetal echocardiography," Ultrasound in Medicine and Biology, NY, NY, US LNKD- DOI:10.1016/S0301-5629(00)00315-X, vol. 27, No. 1, Jan. 1, 2001, pp. 51-59, XP004295664.

* cited by examiner

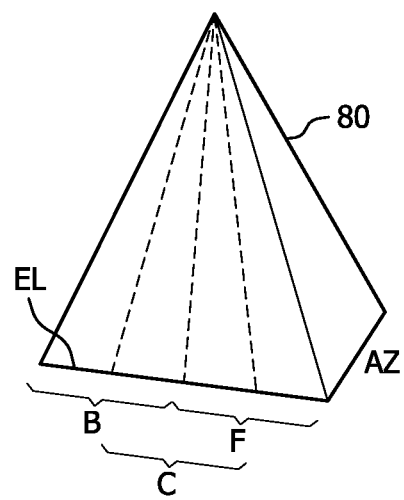
FIG. 5
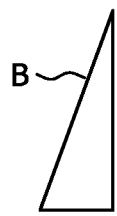  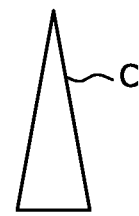  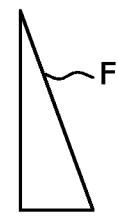
FIG. 6a    FIG. 6b    FIG. 6c

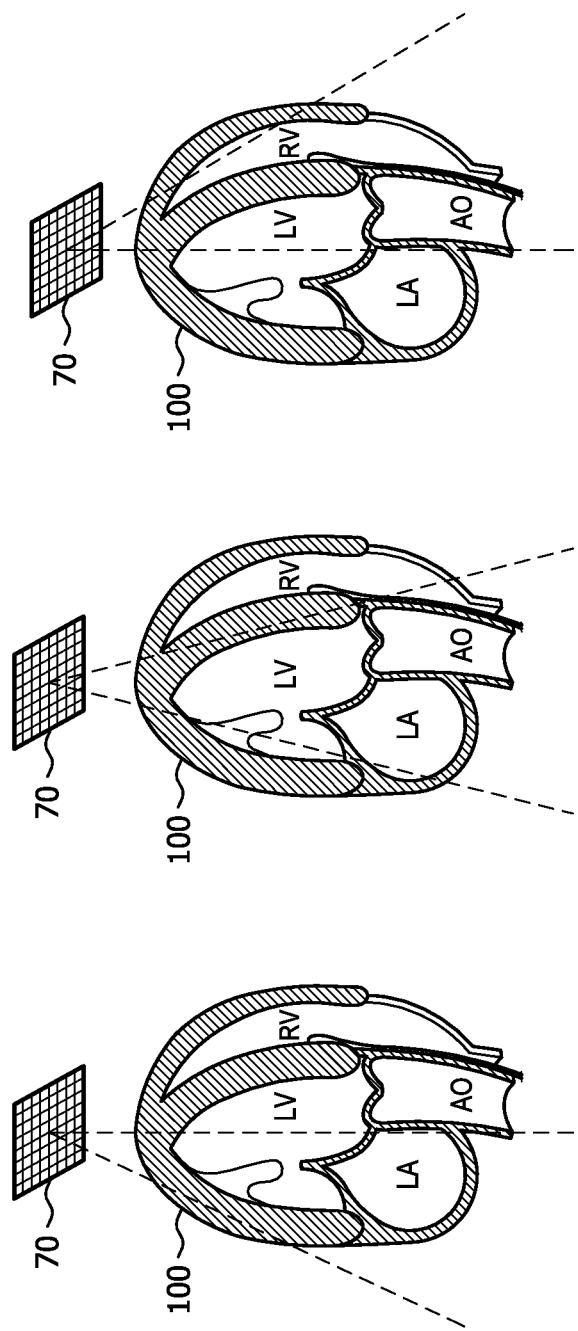

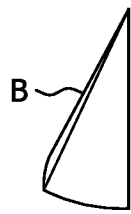
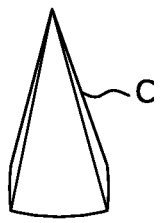
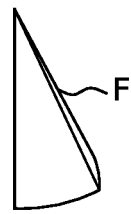
FIG. 8a   FIG. 8b   FIG. 8c
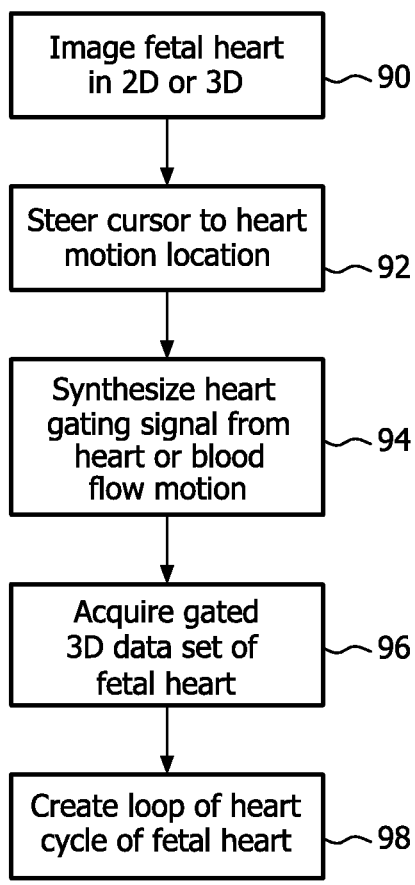
FIG. 9

THREE DIMENSIONAL FETAL HEART IMAGING BY NON-ECG PHYSIOLOGICAL GATED ACQUISITION

This application claims the priority of international application number PCT/IB2010/052469, filed Jun. 2, 2010, which claims the benefit of U.S. provisional application Ser. No. 61/221,885, filed Jun. 30, 2009.

This invention relates to medical diagnostic ultrasound systems and, in particular, to ultrasound systems which acquire three dimensional (3D) image data sets of the fetal heart.

Ultrasound is well suited for fetal imaging because it performs noninvasive imaging without exposing either the mother or the fetus to ionizing radiation. An objective of many fetal examinations is to assess the development of the fetal anatomy to determine whether the fetus is developing normally. As ultrasound image quality has improved over the years, more areas of the anatomy can be visualized for development assessment and in greater detail. Consequently fetal ultrasound exams have become more thorough with increased requirements for anatomy which is to be inspected. One area of the anatomy which is greatly scrutinized is the developing fetal heart. In recent years the outflow tracts of the heart have become a focus of greater attention. The cardiac outflow tracts of the fetal heart can be difficult to image, however. One reason for this is the small size of this fetal anatomy. Another reason is that it is desirable to not simply view the anatomy, but also the dynamics of the flow characteristics through the outflow tracts over the full fetal heart cycle. A further reason is that the outflow tracts undergo considerable development as the fetus grows, and consequently can have varying appearances and complexity depending on fetal age. The outflow tracts can thus be difficult to identify on the ultrasound display, and it can be even more difficult to acquire an image frame of the proper orientation for an adequate diagnosis.

Some of these demands have been eased by the recent use of 3D ultrasound to image the fetal heart. With 3D imaging, the full fetal heart can be imaged and a sequence of 3D image data sets can be acquired for later replay and diagnosis. When data of the full fetal heart is acquired in the data sets, the image data can be examined during post-acquisition diagnosis to locate the outflow tracts of the heart. Different varying 2D image planes can be extracted from the 3D data in multiplanar reconstruction (MPR), so that an image plane of a desired orientation can be examined. Three dimensional imaging thus addresses many of the static imaging challenges which are problematic with 2D fetal imaging. Recently the problem of analyzing the temporal dynamics of fetal blood flow have been addressed by a technique called "spatial-temporal image correlation," or STIC. With STIC, a sweep is made through the fetal heart with ultrasound and many image frames are acquired over a sequence of heart cycles. When done by manually scanning with a 2D ultrasound probe, this image acquisition can take ten seconds or longer. The same acquisition can be performed with a mechanical 3D probe which mechanically sweeps the image plane through the fetal heart region, but 3D mechanical probes often have poorer elevation focus which leads to inaccuracies when constructing MPR images in the elevation dimension. After the acquisition is complete and the image frames are stored, image frames of the desired anatomy, created by MPR reconstruction if necessary, are reassembled into a loop of images according to their phase sequence in the fetal heart cycle. This task is made difficult by the fact that no ECG signal of the fetal heart is available for this reordering. A fetal ECG cannot be acquired during imaging since ECG electrodes cannot be attached to the fetus and the fetal electrical impulses are overwhelmed by the mother's own ECG signals. Consequently it is necessary to extract a synthetic timing signal of the fetal heart cycle from the fetal heart images. This is done by determining event triggers based on fetal tissue movement at or near the heart as described in U.S. Pat. No. 7,261,695 (Brekke et al.) The synthetic heart cycle trigger signals are then used to reorder the images from multiple heart cycles into one loop of a heart cycle in which the frames are in heart beat phase order.

The STIC technique is not without its difficulties however. One is the robustness of the reassembly algorithm. Since the typical acquisition creates far too many images to reorder manually, algorithms have been developed to do the reordering of the frames automatically. These algorithms are dependent upon image data quality, which can be less than adequate. Efforts have been made to improve this situation by using recommended manipulation of the probe to acquire optimal data sets, but this is technique-dependent and it use of anatomical statistics can cause it to be individual patient-dependent. But a greater problem yet is that the fetus frequently moves and may not remain stationary during the full ten or more seconds needed for data acquisition. When the fetus moves the orientation of the desired image data relative to the probe will change, and may leave the field of view entirely, resulting in an absence of the desired anatomy from the acquired data set. Also, fetal movement during the acquisition limits the accuracy of the derived synthetic fetal heart cycle, which introduces artifacts into the reconstructed 3D data. Accordingly it is desirable to overcome these difficulties in fetal heart imaging in general, and those presented by the STIC technique in particular.

In accordance with the principles of the present invention, a diagnostic ultrasound system is described which acquires 3D fetal heart data sets gated to the fetal heart cycle by a physiologically derived gating signal. The fetal heart is imaged by either 1D, 2D or 3D imaging and echo signals from a target exhibiting suitable motion are acquired. For fetal heart imaging the target could be the heart muscle of the fetus or motion of blood in the fetal carotid artery, for example. The motion signals are processed to produce a gating signal synchronized to the fetal heart cycle, which is used to gate 3D image data acquisition. Three dimensional data sets are then acquired in timed relation to the phase of the fetal heartbeat using this physiologically derived gating signal. Gating of acquisition in 3D is much easier to achieve with a 2-dimensional matrix transducer incorporating a micro-beamformer, since in this case imaging planes can be generated electronically in any sequence or orientation. Using such a matrix transducer, a loop of a heart cycle can generally be acquired in less than one second and several loops can be acquired in only a few seconds. Since the acquired image data is already in phase with the fetal heart cycle there is no need to reorder the image data, and since the acquisition takes only a few seconds, fetal movement is less of a concern. One other advantage of this approach, compared to STIC, is that the user can be presented with reconstructed images that show the quality of the acquisition, so that the use can decide if any motion artifacts are present before completing the data acquisition. If the fetus does move during the short acquisition interval the probe can be repositioned and another 3D data acquisition performed. The successfully acquired 3D data can thereafter be carefully analyzed during post-acquisition diagnosis.

In the drawings:

FIG. 5 illustrates the division of the volumetric region of FIG. 4 into three sub-regions.

FIGS. 6a, 6b, and 6c illustrate image planes of the three sub-regions of FIG. 5.

FIGS. 7a, 7b, and 7c illustrate the scanning of three volumetric sub-regions of the heart by a matrix array transducer.

FIGS. 8a, 8b, and 8c illustrate the three sub-volumes of image data acquired by the scanning sequence of FIG. 7.

FIG. 9 illustrates a method for acquiring a 3D data set of the fetal heart using a physiologically derived heart cycle gating signal.

Figure 1:
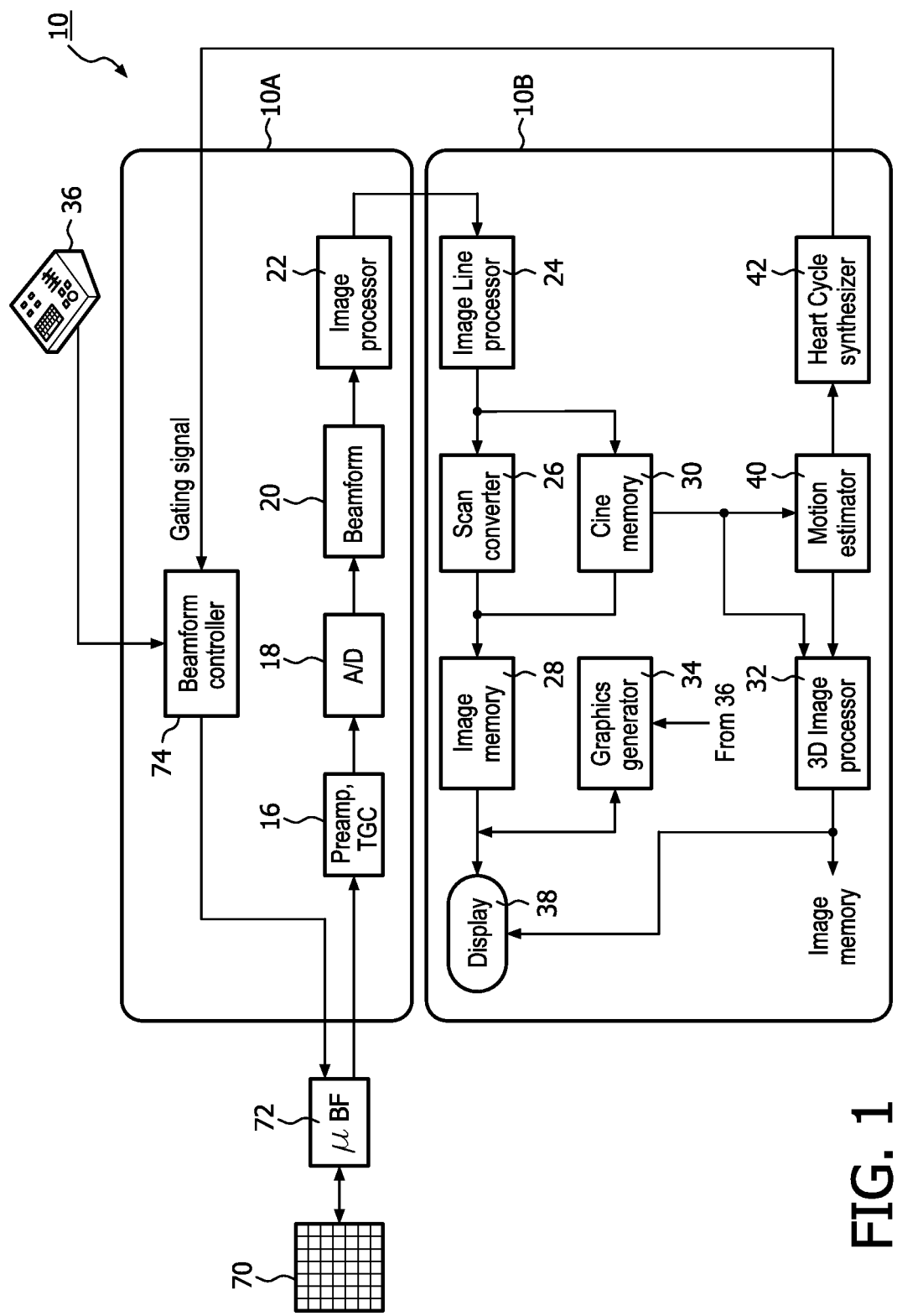
FIG. 1 illustrates in block diagram form an ultrasonic diagnostic imaging system constructed in accordance with the principles of the present invention.

Referring first to FIG. 1, an ultrasound system 10 constructed in accordance with the principles of the present invention is shown in block diagram form. The ultrasound system is configured by two subsystems, a front end acquisition subsystem 10A and a display subsystem 10B. An ultrasound probe is coupled to the acquisition subsystem which includes a two-dimensional matrix array transducer 70 and a micro-beamformer 72. The micro-beamformer contains circuitry which control the signals applied to groups of elements ("patches") of the array transducer 70 and does some processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque).

The probe is coupled to the acquisition subsystem 10A of the ultrasound system. The acquisition subsystem includes a beamform controller 74 which is responsive to a user control 36 and provides control signals to the microbeamformer 72, instructing the probe as to the timing, frequency, direction and focusing of transmit beams. The beamform controller also control the beamforming of echo signals received by the acquisition subsystem by its control of analog-to-digital (A/D) converters 18 and a beamformer 20. Echo signals received by the probe are amplified by preamplifier and TGC (time gain control) circuitry 16 in the acquisition subsystem, then digitized by the A/D converters 18. The digitized echo signals are then formed into fully steered and focused beams by a beamformer 20. The echo signals are then processed by an image processor 22 which performs digital filtering, B mode and M mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format. The echo signals are processed by an image line processor 24, which is capable of sampling the echo signals, splicing segments of beams into complete line signals, and averaging line signals for signal-to-noise improvement or flow persistence. The image lines for a 2D image are scan converted into the desired image format by a scan converter 26 which performs R-theta conversion as is known in the art. The image is then stored in an image memory 28 from which it can be displayed on a display 38. The image in memory is also overlaid with graphics to be displayed with the image, which are generated by a graphics generator 34 which is responsive to the user control 36. Individual images or image sequences can be stored in a cine memory 30 during capture of image loops or sequences.

For real-time volumetric imaging the display subsystem 10B also includes a 3D image rendering processor 32 which receives image lines from the image line processor 24 for the rendering of real-time three dimensional images. The 3D images can be displayed as live (real time) 3D images on the display 38 or coupled to the image memory 28 for storage of the 3D data sets for later review and diagnosis.

Figure 2:
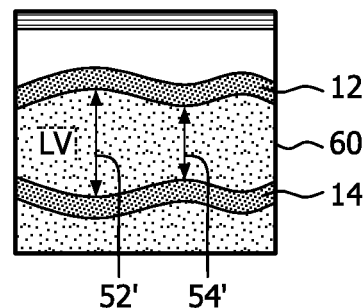
FIG. 2 illustrates an M mode image of the motion of the heart muscle.

In accordance with the principles of the present invention a motion estimator 40 receives temporally discrete echo signals from a designated location of the imaged anatomy and processes the echoes to produce a signal representative of motion at the designated location. The location in the anatomy from which the temporally discrete echo signals are acquired can be a default image location such as the center of the image, or it can be a location designated by the user by manipulation of a control of the user controls 36. For instance, the user can manipulate a joystick, trackball, or other control of the user controls to locate a sample volume in the carotid artery of the fetus. Motion estimation can then be performed from samples of the moving fetal tissue or blood. Some of this processing may be performed by the image processor, such as Doppler processing of echo signals from the sample volume location. Flow or tissue motion velocity estimates produced by the image processor can then be forwarded directly to the motion estimator, for example. If the sample volume is placed on tissue such as the fetal heart muscle, the echo signals from the fetal heart can be processed for motion discrimination by tissue Doppler processing. Another way to detect motion is by tracking the movement of speckle at a given tissue location in the image. Yet another way to detect motion is by comparing changes in tissue location over consecutive images by MSAD block matching as described in U.S. Pat. No. 6,299,579 (Peterson et al.) Still another technique for detecting motion is to use M mode with the M line positioned through the fetal heart. This is illustrated in FIG. 2, which shows an M mode image 60 produced by an M line located by positioning the M line cursor on the ultrasound image so that it extends through the left ventricle (LV) of the fetal heart. When positioned in this manner the M line will pass through the myocardial wall 12 on one side of the fetal heart, through the chamber of the LV, and through the myocardial tissue 14 on the other side of the heart. An ultrasound beam is transmitted along this M line direction through the LV periodically, and the received A-line from each transmission is shown on the display in a scrolling manner along the previously received A-lines. The result is an M mode image as shown in FIG. 2 where the opposite sides of the heart are most greatly separated when the fetal heart is relaxed at the end diastole point in the heart cycle as indicated by arrow 52'. The opposite walls of the heart are in closest proximity at the peak systole phase of the heart cycle as indicated by arrow 54'. FIG. 2 illustrates this cyclical pattern of the movement of the heart wall as the fetal heart contracts and expands with each heart beat. By tracking the changing position (motion) of the heart wall 12 or 14, a waveform in phase with the heart cycle can be produced.

While the location for motion detection may be designated in a two or three dimensional image, it is preferred to use a 2D image for its higher frame rate and therefore higher sampling rate. An M line for location designation using M mode as illustrated by FIG. 2 can provide an even greater sampling rate. The location of the sample volume, M line, or other cursor which is selected by a user control 36 is coupled to the graphics generator 34 so that the location can be continuously updated and displayed in the ultrasound image that the user is viewing while positioning the cursor. In an embodiment of the present invention it is necessary that the motion being estimated be related to the motion of the beating fetal heart. Thus, the moving fetal heart muscle and blood flow in the fetal carotid artery provide excellent sources of echo signals for fetal heart-related motion detection.

Figure 3:
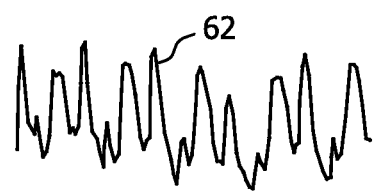
FIG. 3 illustrates a heart gating waveform produced from heart motion.
Figure 4:
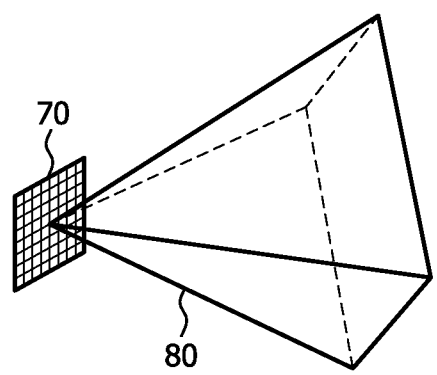
FIG. 4 illustrates a volumetric region which is scanned by a two dimensional matrix array transducer.

The signals representing the detected motion are coupled to a heart cycle synthesizer which produces signals representative of the fetal heart cycle. The fetal heart cycle signals can be a continuous sequence of signals approximating a waveform 62 such as that shown in FIG. 3, which is a heart waveform produced from a sample volume by power motion imaging processing as described in U.S. Pat. No. 5,718,229 (Pesque et al.) whereby consecutive echoes from a sample volume location are differentiated (subtracted) to detect signal changes indicative of motion. The waveform may be smoothed as desired to assume a more repetitive, consistent shape. The waveform signals may be used to indicate gating times for successive phases of the heart cycle. Alternatively, the heart cycle signals can be produced only at desired gating times when a fetal heart image is to be acquired at a predetermined phase of the heart cycle. For instance, if a sequence of images acquired at end diastole are desired, a gating signal would be produced only at that time in each heart cycle. In the example of FIG. 2, this would be the time in each heart cycle when the spacing of the heart walls was at its greatest as shown by arrow 52'. The heart cycle signals are applied to the beamform controller 74 where they are used to gate the acquisition of fetal heart images at the desired times during the fetal heart cycle. Since a sequence of images may now be gated for acquisition at known phases of the heart cycle, there is no need to try to retrospectively estimate the acquisition timing as is done in STIC, and there is no need for reordering of the images since they acquired and thus are already arranged in heart cycle phase order.

The time and the technique used to acquire 3D data sets of the fetal heart depend on the extent of the anatomy which is to be scanned. If the volumetric region from which 3D data sets are to be acquired is relatively small, it may possible to acquire the 3D data sets in a single volumetric sweep. This means that a sequence of images for replay as live images of a full heart cycle can be acquired in a single heart cycle. Since the fetal heart rate is generally much higher than that of a child or adult, this means that the necessary 3D data sets of a full heart beat can be acquired in less than one half of a second.

When the volumetric region is large, the volume may be scanned in successively acquired subvolumes, which are then aggregated for replay as a live image of the full volume, as described in U.S. Pat. No. 5,993,390 (Savord et al.) 3D data sets of each subvolume are acquired over a complete heart cycle. The subvolumes are then spatially aligned and replayed in heart phase synchronism. The phase synchronism of acquisition and replay can thus rely on the physiologically derived heart phase gating signal of the present invention. This segmented, full volume technique is illustrated by FIGS. 4-8, FIG. 4 illustrates a full volumetric region 80 which is scanned by phased array operation of a matrix array transducer 70 by the ultrasound system 10 of FIG. 1. In this example the full volume is in the shape of a rectangular pyramid. The height of the pyramid from its apex to its base determines the depth of the region being imaged, which is chosen in accordance with factors such as the frequency and depth of penetration of the beams. The inclination of the sides of the pyramid are determined by the degree of steering applied to the beams, which in turn are chosen in consideration of the delays available for beam steering and the sensitivity of the transducer to off-axis (acutely inclined) beam steering, among other considerations.

A full volumetric region such as volumetric region 80 may be of sufficient size to encompass the entire fetal heart for 3D imaging. However the time required to scan the entire full volumetric region 80 to visualize the entire heart may be too slow for satisfactory real time imaging, or may take too long such that motion artifacts occur, or both. To overcome these limitations, the full volumetric region 80 is divided into subvolumes B (back), C (center) and F (front), as shown in FIG. 5. While the volumetric region 80 may subtend an angle in the azimuth (AZ) direction of 60% for instance, the subvolumes will subtend lesser angles. In the example of FIG. 5 the subvolumes each subtend an angle of 30°. This means that, for the same beam density and depth, each subvolume can be scanned in half the time of the entire volumetric region 80. This will result in a doubling of the real time frame rate of display. The subvolumes can be made contiguous or overlapping. For example, if the angle of the full volumetric region were 90% three contiguous subvolumes of 30° each might be employed. Alternatively, for a 60° full volumetric region, three 20° subvolumes could be used for an even higher frame rate. In the example of FIG. 5 the B and F subvolumes are contiguous in the center of the full volumetric region 80 and the C subvolume is centered at the center of the region 80, providing a 50% overlap of contiguous subvolumes. If a plane were acquired of each of the B, C, and F subvolumes, either by direct scanning or MPR reconstruction, the planes would have the shapes as shown in FIGS. 6a, 6b, and 6c.

The subvolumes B, C, and F are scanned over a complete heart cycle, in either one continuous interval or smaller, time-interleaved intervals, as shown in FIGS. 7a, 7b, and 7c. FIG. 7a shows the B subvolume being scanned by the matrix array transducer 70, which in this example acquires 3D data sets of the left atrium and part of the left ventricle. FIG. 7b shows the C subvolume being scanned, which in this example acquires 3D data sets of the rest of the LV, most of the left atrium, and the aorta. FIG. 7c shows the F subvolume being scanned, which acquires 3D data sets of the right part of the LV, the aorta, and the right ventricle. Thus, the three subvolumes acquire 3D data sets of virtually the entire heart and over a complete heart cycle. FIGS. 8a, 8b, and 8c illustrate 3D images of each subvolume. When the three subvolumes are merged together in spatial alignment and replayed in phase synchronism, the entire fetal heart can be seen in a live 3D image loop of a complete heart cycle. The replay can be stopped to closely examine the heart in 3D at any point in the heart cycle, and selected planes through the volume can be reconstructed by MPR to analyze the fetal heart is selected 2D (planar) views.

Regardless of how many sub-volumes are acquired, or the amount of overlap, another benefit of a time-gated acquisition of sub-volumes is that the user may be presented with a full volume of data that is updated in pseudo real-time, similar to the concepts described in U.S. Pat. No. 5,993,390 (Savord et al.) and U.S. Pat. No. 5,099,847 (Powers et al.) This can be achieved by generating a full volume as soon as one full set of sub-volumes have been acquired, and then cycling through the sequence of sub-volumes, updating the full volume every time a new sub-volume is acquired. In this way, a full volume image is presented to the user at the higher sub-volume rate, thus allowing the user to either evaluate the fetal heart dynamically (in pseudo real-time), or alternatively decide dynamically when a good quality full volume image has been acquired and storing it for later review.

FIG. 9 illustrates a procedure for acquiring 3D data sets for a live 3D image loop of the fetal heart. In step 90 the fetal heart is imaged in real time 2D or 3D imaging for placement of a motion estimate location of this is not done automatically. If it is desired to closely examine the fetal outflow tract, for instance, the outflow tract would be prominently included in the image area. In step 92 the clinician steers a cursor in the ultrasound image to a location where heart motion is to be estimated. This could comprise placing a sample volume on moving heart tissue, in the blood flow of the fetal carotid artery, or locating an M line to intersect the myocardium of the fetal heart, for example. In step 94 the motion estimator and the heart cycle synthesizer have synthesized a heart gating signal from the indicated motion of the heart or blood flow. In step 96 the heart gating signal is used to acquire one or more gated 3D data sets of the heart or a region of interest in the heart such as the outflow tracts. This could be done automatically as soon as the heart gating signal has stabilized, or it could be done on command by the clinician. For instance, if the fetus is moving the clinician may reposition the probe until the desired fetal heart anatomy is in the center of the image. When the clinician has the target anatomy positioned in the image field as desired, she pushes a button on the control panel 36 to command the system to acquire data. When the heart gating signal is sufficiently stable the ultrasound system would then acquire the necessary gated 3D data sets for diagnosis. A full volume data set of the heart acquired in three subvolumes as illustrated in FIGS. 5-8 can usually be acquired in less than two seconds. Thus, if the fetus remains stationary for as little as two seconds, 3D data sets of diagnostic quality of the fetal heart can be successfully acquired. In step 98 a live 3D image loop of the fetal heart is created from a single acquired 3D data set, or by combining the 3D data sets of subvolume acquisitions.

It will be apparent that the present invention will have applicability for other types of exams in addition to fetal cardiology exams. For instance, a radiology department may not have ECG equipment for a gated vascular exam. The techniques of the present invention may then be used to develop acquisition gating signals for a vascular exam.

What is claimed is:

1. An ultrasonic diagnostic imaging system for analyzing a fetal heart, the system comprising:
a single 3D ultrasound imaging probe having a two-dimensional matrix array transducer and a micro-beamformer operable to acquire 3D image data sets of the fetal heart and M mode echo signals from a selectably positioned M line intersecting the fetal heart, the 3D imaging probe configured to transmit beams along the M line and acquire the M mode echo signals generated in response to the transmitted beams;
a user control configured to, in response to user input, selectably position the M line by positioning an M line cursor which designates a location of motion in fetal heart anatomy in a displayed ultrasound image which is representative of a fetal heart cycle;
a motion estimator responsive to the acquired M mode echo signals from the designated location in the fetal heart anatomy, the motion estimator configured to process the M mode echo signals to produce an estimate of motion of moving fetal tissue or blood and produce a gating signal in relation to the fetal heart cycle based on the estimated motion of the moving fetal tissue or blood;
a probe controller responsive to the gating signal and configured to cause the two-dimensional matrix array transducer of the 3D imaging probe to acquire the 3D image data sets at one or more predetermined phases of the fetal heart cycle as determined by the gating signal;
an image processor configured to receive the 3D image data sets and process the received 3D image data sets to generate a 3D image of the fetal heart; and
a display configured to display the 3D image of the fetal heart.

2. The ultrasonic diagnostic imaging system of claim 1, wherein the motion estimator is further responsive to 2D image echo signals acquired using the two-dimensional matrix array transducer to produce the gating signal.

3. The ultrasonic diagnostic imaging system of claim 1, wherein the probe controller is further responsive to the gating signal to cause the two-dimensional matrix array transducer of the 3D imaging probe to acquire subvolume 3D data sets of a volumetric region which includes the designated location; and further comprising a subvolume processor which is operative to update a 3D image volume with newly acquired subvolume 3D data sets.

4. The ultrasonic diagnostic imaging system of claim 3, wherein the display is operative to display 3D images of the 3D image volume at a frame rate which is faster than a time required to acquire all of the subvolumes for a full image volume.

5. A method of acquiring gated ultrasonic 3D fetal heart images with a synthetic gating signal, the method comprising:
imaging a fetal heart using a single 3D ultrasonic imaging probe comprising a two dimensional matrix array transducer coupled to a probe micro-beamformer;
steering a cursor to a location of fetal heart motion on a displayed ultrasound image;
acquiring, using the 3D ultrasonic imaging probe, 2D or 3D echo signals from the location of fetal heart motion;
synthesizing a gated acquisition signal based on motion detected in motion images generated from the 2D or 3D echo signals acquired from the location of fetal heart motion, wherein the motion is detected by one of speckle tracking or block matching in the generated motion images;
acquiring gated 3D data sets of the fetal heart by causing the two dimensional matrix array transducer of the 3D ultrasonic imaging probe to acquire 3D data sets at one or more predetermined phases of a cycle of the fetal heart as determined by using the synthesized gated acquisition signal; and
forming, using a processor, a sequence of dynamic 3D fetal heart images from the gated 3D data sets.

6. The method of claim 5, wherein acquiring the 2D or 3D echo signals further comprises acquiring echo signals by B mode image acquisition.

7. The method of claim 5, wherein acquiring gated 3D data sets further comprises acquiring 3D subvolume data sets of a 3D volume which includes the fetal heart.

8. The method of claim 7, wherein forming the sequence of dynamic 3D fetal heart images further comprises combining multiple 3D subvolume data sets to form a 3D fetal heart image.

9. An ultrasonic diagnostic imaging system for acquiring live 3D images of a moving anatomy in absence of an anatomical gating signal comprising:
a single 3D imaging probe having a two-dimensional matrix array transducer and a micro-beamformer operable to acquire 3D image data sets of the moving anatomy;
a user control configured to, in response to user input, locate an M line by positioning an M line cursor which designates a location of motion in a displayed ultrasound image of the moving anatomy, wherein the 3D imaging probe is configured to transmit beams along the M line and receive M mode echo signals from the moving anatomy;

a motion estimator responsive to the received M mode echo signals from moving tissue or blood at the designated location of motion and configured to process the M mode echo signals to produce an estimate of motion of the moving anatomy and to produce a gating signal in relation to the estimated motion of the moving anatomy;

a probe controller responsive to the gating signal and configured to cause the 3D imaging probe to acquire gated 3D data sets at one or more predetermined phases of a motion cycle of the moving anatomy as determined by the gating signal;

an image processor configured to receive the 3D data sets and process the received 3D data sets to generate a dynamic 3D image sequence of the moving anatomy; and a display configured to display the dynamic 3D image sequence of the moving anatomy.

10. The ultrasonic diagnostic imaging system of claim 9, wherein the user control is configured to be manipulated to designate a location of motion in a 2D or 3D ultrasound image.

11. The ultrasonic diagnostic imaging system of claim 9, wherein the motion estimator is further responsive to B mode echo signals from the designated location.

12. The ultrasonic diagnostic imaging system of claim 9, wherein the probe controller is further responsive to the gating signal to cause the imaging probe to acquire gated 3D data sets of subvolumes of a volumetric region of the moving anatomy.

13. The ultrasonic diagnostic imaging system of claim 12, further comprising a subvolume processor which is operative to update a 3D image with newly acquired subvolume 3D data sets.

* * * * *